(12) United States Patent
Holyfield

(10) Patent No.: US 9,060,946 B2
(45) Date of Patent: Jun. 23, 2015

(54) TOPICAL SKIN CARE FORMULATIONS

(71) Applicant: Louise Holyfield, Dallas, TX (US)

(72) Inventor: Louise Holyfield, Dallas, TX (US)

( * ) Notice: Subject to any disclaimer, the term of this patent is extended or adjusted under 35 U.S.C. 154(b) by 0 days.

(21) Appl. No.: 13/999,849

(22) Filed: Mar. 27, 2014

(65) Prior Publication Data
US 2015/0064125 A1 Mar. 5, 2015

Related U.S. Application Data

(63) Continuation-in-part of application No. 13/987,737, filed on Aug. 27, 2013.

(51) Int. Cl.
| | | |
|---|---|---|
| *A61K 8/00* | (2006.01) | |
| *A61K 8/35* | (2006.01) | |
| *A61K 8/34* | (2006.01) | |
| *A61Q 1/02* | (2006.01) | |
| *A61Q 19/08* | (2006.01) | |
| *A61K 8/04* | (2006.01) | |
| *A61Q 17/04* | (2006.01) | |

(52) U.S. Cl.
CPC ............... *A61K 8/355* (2013.01); *A61K 8/347* (2013.01); *A61Q 1/02* (2013.01); *A61Q 19/08* (2013.01); *A61K 8/04* (2013.01); *A61Q 17/04* (2013.01); *A61K 8/35* (2013.01); *A61K 2800/42* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,393,045 | A * | 7/1983 | Henderson et al. | 424/547 |
| 4,714,609 | A * | 12/1987 | Carden | 424/59 |
| 2009/0269375 | A1* | 10/2009 | Patnode | 424/401 |
| 2011/0020252 | A1* | 1/2011 | Shantha et al. | 424/59 |
| 2012/0177586 | A1* | 7/2012 | Mehta et al. | 424/59 |

* cited by examiner

*Primary Examiner* — Hasan Ahmed
(74) *Attorney, Agent, or Firm* — Gary C. Honeycutt

(57) ABSTRACT

A white, color-stable, stain-free emulsion formulation containing vanillin for sunless tanning. The amount of vanillin can be adjusted, from about 1% up to about 45%, to provide light or dark tanning of the skin. Lime oil and lime juice form a preferred white emulsion foundation.

8 Claims, No Drawings

TOPICAL SKIN CARE FORMULATIONS

FIELD OF INVENTION

This invention relates to chemical and natural compositions, and more particularly to topical anti-aging, anti-oxidant skin care formulations and methods of use.

BACKGROUND OF THE INVENTION

For thousands of years people have been conscious of the need for skin care for various reasons, including cleanliness, comfort, beauty, and protection against the sun. Research has confirmed the benefits of proper skin care through the use of products that contain anti-aging ingredients, primarily anti-oxidants and sunscreens.

Consumers, both men and women regardless of age, are particularly interested in products that contain anti-aging, anti-oxidant topical creams and lotions that beautify and protect the skin from free radicals and stress oxidation. Anti-oxidants and sunscreens are the skin's first defense in fighting free radicals that are in the form of ionic particles that persist in the atmosphere. Free radicals have the ability to; permeate the skin and lungs thereby damaging skin cells/DNA.

Since world population grows exponentially, there is every indication that the demand for skin care products that both beautify and protect the skin will continue to grow. No one can dispute the fact that we live in a society that admires beauty. Hundreds of billions of dollars are spent annually in the global beauty industry, and as the consumer economic base grows in China, India and other countries throughout the world, the demand for skin care products will increase exponentially.

As we learn more about the aging process, coenzyme Q10 ranks as one of the most, if not the most, powerful and effective topical anti-oxidants when used at a percentage level that is known to be effective to protect the skin against free radicals. The beauty industry has been unable to fully utilize CoQ10 because it is not white and not color-stable. Consumers have a strong preference for white, color-stable products, but when CoQ10 is used at an effective percentage level in an aqueous emulsion product, it degrades the formulation into various shades of orange or brown. Such an unstable product is commercially unacceptable because it is perceived to be impure or contaminated.

Vanillin is another natural, powerful and effective anti-aging, antioxidant ingredient that is used in the pharmaceutical and beauty industry. Vanillin has also been recognized as a tanning agent for the skin. See U.S. Pat. Nos. 4,714,609 and 7,935,331. But, similarly as with CoQ10, the industry has been unable to fully utilize vanillin due to the instability of its color in aqueous emulsion products. Although vanillin is naturally white in color it quickly degrades into various shades of brown when used in aqueous emulsion products. Vanillin's optimum benefits cannot be fully realized until it is available in a white, color-stable emulsion product.

There is an urgent need for preserving the whiteness of products containing CoQ10 and vanillin. White is the commercially preferred color for any product used on the face and body. To optimize the use of these two natural, powerful, as effective anti-aging, antioxidant ingredients, it is imperative that products containing CoQ10 and vanillin be white in color and remain white throughout the shelf life of the product.

The utilization of these two powerful and effective antioxidant ingredients can be enormously effective in anti-aging and sun and sunless tanning products, thereby eliminating the need to overexpose ones skin in the sun, while creating an antioxidant barrier that can will help prevent skin cancer caused by free radicals that permeate and damage the skin (DNA).

SUMMARY OF THE INVENTION

One aspect of this invention provides a white, color-stable topical anti-aging, anti-oxidant skin care formulation comprising 1) an effective amount of a benzoquinone, such as CoQ10, and 2) an effective amount of vanillin, or a derivative thereof, such as ethyl vanillin, combined in an aqueous emulsion formulation that is white in color and remains white for the shelf life of the product.

A second aspect of the invention provides a white, color-stable topical anti-aging, anti-oxidant skin care formulation comprising an effective amount of a benzoquinone, such as CoQ10, in an aqueous emulsion formulation that is white in color and remains white for the shelf life of the product.

A third aspect of the invention provides a white, color-stable topical anti-aging, anti-oxidant skin care formulation comprising an effective amount of vanillin, or a derivative thereof, such as ethyl vanillin, in an aqueous emulsion formulation that is white in color and remains white for the shelf life of the product.

A fourth aspect of the invention provides a white, color-stable topical sun or sunless tanning, anti-aging, anti-oxidant skin care formulation comprising 1) an effective amount of a benzoquinone, such as CoQ10, and 2) an effective amount of vanillin, or a derivative thereof, such as ethyl vanillin, to be combined in an aqueous emulsion product formulation that is white in color and will remain white for the shelf life of the product.

A fifth aspect of the invention provides a white, color-stable topical sun or sunless tanning, anti-aging, anti-oxidant sunscreen formulation comprising 1) an effective amount of a benzoquinone, such as CoQ10, and 2) an effective amount of vanillin, or a derivative thereof, such as ethyl vanillin, combined in a lime emulsion product formulation that is white in color and will remain white for the shelf life of the product.

A sixth aspect of the invention provides a white, color-stable topical anti-aging, anti-oxidant skin care formulation comprising of (1) an effective amount of a benzoquinone, such as CoQ10, and 2) an effective amount of vanillin, or a derivative thereof, such as ethyl vanillin, combined in a lime emulsion (lime juice and lime oil) product formulation that is white in color and will remain white for the shelf life of the product.

A seventh aspect of the invention provides a white, color-stable topical anti-aging, anti-oxidant skin care formulation comprising an effective amount of a benzoquinone, such as CoQ10, to be used in a lime emulsion (lime juice and lime oil) product formulation that is white in color and remains white for the shelf life of the product. The lime emulsion (lime oil in lime juice) is superior to other emulsions, because it is more effective to enhance initial whiteness, and more effective to prolong color stability. A product containing CoQ10 in a lime emulsion (lime juice and lime oil) can be applied to the overall face and body to provide protection from free radicals that permeate the skin and damage the skin (DNA).

An eighth aspect of the invention provides a white, color-stable topical anti-aging, anti-oxidant skin care formulation comprising an effective amount of vanillin, or a derivative thereof, such as ethyl vanillin, in a lime emulsion (lime juice and lime oil) product formulation that is white in color and remains white for the shelf life of the product.

A ninth aspect of the invention provides a white, color-stable topical sun or sunless tanning, anti-aging, antioxidant skin care formulation comprising 1) an effective amount of a benzoquinone, such as CoQ10, and 2) an effective amount of vanillin, or a derivative thereof, such as ethyl vanillin, and 3) and an SPF 30+, combined in a lime emulsion (lime juice and lime oil) product formulation that is white in color and will remain white for the shelf life of the product.

The application of a topical product comprising of CoQ10 and vanillin in a lime emulsion (lime juice and lime oil) onto the face and body delivers a high degree of anti-aging antioxidants that will penetrate the skin to work at a cellular level. The skin will turn a beautiful golden brown color within 6 to 12 hours and can continue to turn the skin a little darker for up to twenty-four hours. With the inclusion of a SPF 30+, the skin will have further protection while in the sun. If the user wishes to avoid the sun they can go about their business and tan regardless of the environment. The tan will appear once it reaches the skin's cellular level whether a person is in the light or in total darkness.

The percentages of vanillin in a lime emulsion formula determine the shade of tan that is obtained on the skin. For example, a light golden brown is obtained using 6 wt % vanillin; while a dark golden brown is obtained using 18 wt % vanillin. Within 4 to 6 hours after application of the product the skin begins to look tan as the vanillin reaches the cellular level. The skin color reaches maximum darkness, based upon color selection, within 12 to 24 hours. The tanning products do not streak on the skin, nor rub off on clothing. Clothing can be worn immediately after application of the products, without fear of staining the clothes.

Once the product has been applied to the face, body, or other desired areas, the user can go about their normal routine. The tanning process will continue, in the sun, in the shade, or total darkness, regardless of the environmental conditions. The tan normally lasts 10 to 15 days, without further care. Also, the tan can be maintained for longer periods of time by daily use of a maintenance formula containing 3 wt % CoQ10 and 3 wt % vanillin in a lime emulsion.

If protection against the sun is also desired, sunscreens can be added to the maintenance formula, in amounts that are effective to provide the necessary or desired SPF rating. Cosmetics or makeup can also be safely used on the skin immediately following the application of any of the products of the present invention.

A tenth aspect of the invention provides a white, color-stable topical anti-aging, anti-oxidant skin care formulation comprising an effective amount of a benzoquinone, such as CoQ10, in a lime emulsion (lime juice and lime oil) formulation that includes a SPF 15+, and that is white in color and remains white for the shelf life of the product An eleventh aspect of the invention provides a white, color-stable topical sun or sunless tanning, anti-aging, anti-oxidant skin care formulation comprising 1) an effective amount of benzoquinone, such as CoQ10, 2) an effective amount of vanillin, or a derivative thereof, such as ethyl vanillin, and a3) an effective SPF 15+, combined in a lime emulsion (lime juice and lime oil) formulation that is white in color and remains white for the shelf life of the product.

A twelfth aspect of the invention provides a white, color-stable topical sun or sunless tanning, anti-aging, anti-oxidant skin care formulation comprising an effective amount of vanillin, or a derivative thereof, such as ethyl vanillin, and an effective SPF 15+, in a lime emulsion (lime juice and lime oil) formulation that is white in color and remains white for the shelf life of the product.

A thirteenth aspect of the invention provides a white, color-stable topical anti-aging, antioxidant product formulation comprising an effective amount of a benzoquinone, such as CoQ10, and an effective amount of vanillin, or a derivative thereof, such as ethyl vanillin, in combination with a lime juice-lime oil emulsion product formulation that is white in color and remains white for the shelf life of the product. By combining effective percentages of CoQ10, vanillin, and SPF ingredients in one formulation, the most powerful anti-aging, antioxidant, sun or sunless tanning product is created. The safety of the ingredients, CoQ10, vanillin, and SPF's, ensures that the benefits of preventing skin cancer and anti-aging are available to anyone, regardless of age.

The individual components of the inventive formulations are well known. As used herein, "CoQ10" is defined to include all the benzoquinones and obvious equivalents. "Vanillin" is defined to include all the obvious equivalents, such as ethyl vanillin and many others.

Lime is a well-known citrus fruit, widely used as a commercial source of lime juice and lime oil. Common emulsifiers are used in the preparation of emulsions from mixtures of lime juice and lime oil. As used in this invention, the preferred lime juice-lime oil emulsions contain about 60-90 wt % juice and about 10-40 wt % oil.

In order to preserve whiteness in products containing CoQ10 or vanillin, or the combination of both, additional ingredients are added to the above formulations. Because of their synergistic effect, the preferred additional ingredients are octyl salicylate and octyl methoxycinnamate. Other suitable ingredients for preserving whiteness include titanium dioxide, zinc oxide, p-aminobenzoic acid (PABA), octyldimethyl-PABA, phenylbenzimidazole sulfonic acid, 2-ethoxyethyl p-methoxycinnamate, dioxybenzone, oxybenzone, homosalate, methyl anthranilate, octocrylene, sulisobenzone, triethanolamine salicylate, avobenzone, and ecamsule. These added ingredients are useful alone, or in combination of two or more.

There are many well-known emulsifiers and methods for preparing cosmetic emulsions, useful in the formulations of the present invention. See for example U.S. Pat. No. 6,906, 106 incorporated herein by reference.

For a suitable list of ubiquinones, related compounds and derivatives, useful in the formulations of the invention, see U.S. Pat. No. 6,906,106 incorporated herein by reference.

For a suitable list of vanillin derivatives and related compounds useful in the formulations of the present invention, see U.S. Pat. No. 7,935,331 incorporated herein by reference. As used herein, "lime emulsion" is defined as lime oil dispersed in lime juice. An "aqueous emulsion" is defined as any other suitable oil dispersed in water.

CoQ10 is used from 0.50% by wt. to 5% by wt. in an aqueous emulsion or in a lime emulsion, or in a combination of both aqueous and lime. Vanillin is used from 0.50% by wt. to 45% by wt. in an aqueous emulsion or in a lime emulsion, or in a combination of both aqueous and lime. Octyl salicylate is used from 1% by wt. to 15% by wt. in an aqueous emulsion or in a lime emulsion, or in a combination of both aqueous and lime. Octyl methoxycinnamate is used from 1% by wt. to 15% by wt. in an aqueous emulsion or a lime emulsion, or in a combination of both aqueous and lime. Titanium dioxide is used from 0.15% to 5% by wt. in an aqueous emulsion or in a lime emulsion, or in a combination of both aqueous and lime. Zinc oxide is used from 0.15% by wt. to 5% by wt. in an aqueous emulsion or in a lime emulsion, or in a combination of both aqueous and lime.

A lime emulsion contains lime oil and preferably from 64% by wt. to 84% by wt. lime juice. An aqueous emulsion contains any suitable oil and preferably from 64% by wt. to 84% by wt. water. Mixtures of aqueous and lime emulsions are also used.

EXAMPLES

A. 3% by wt. CoQ10+3% by wt. vanillin
    4% by wt. octyl salicylate
    4% by wt. octyl methoxycinnamate
    0.50% by wt. titanium dioxide
    0.23% by wt. zinc oxide
    85.17% by wt. white emulsion, including water, oil, and emulsifiers The above formulation, including both CoQ10 and vanillin in an aqueous emulsion, ensures that the product is white in color and remains white; and that the formulation provides a high level of anti-aging, antioxidant benefits along with the ability to lightly tan the skin at a cellular level beginning in 4 to 8 hours of application and continuing for up to 24 hours. The formulation also protects the skin with an SPF factor of 8+ to further minimize free radical damage to the skin (DNA). The formulation will not streak on the skin or stain clothing, including white clothing. The amounts of CoQ10, vanillin, and sunscreens in this example are safe and effective.

B. 4% by wt. CoQ10 +6% by wt. vanillin
    6% by wt. octyl salicylate
    6% by wt. octyl methoxycinnamate
    0.75% by wt. titanium dioxide
    0.38% by wt. zinc oxide
    76.87% by wt. white emulsion, including lime juice, lime oil, and emulsifiers The above formulation, including both CoQ10 and vanillin in a lime emulsion, ensures that the product is white in color and remains white; and that the formulation provides a very high level of anti-aging, antioxidant benefits along with the ability to tan the skin at a cellular level beginning in 4 to 8 hours of application and continuing for up to 24 hours. The formulation also protects the skin with an SPF factor of 15+ to further minimize free radical damage to the skin (DNA). The formulation will not streak on the skin or stain clothing, including white clothing. The amounts of CoQ10, vanillin, and sunscreens in this example are safe and effective.

C. 4% by wt. CoQ10
    2.67% by wt. octyl salicylate
    2.67% by wt. octyl methoxycinnamate
    0.33% by wt. titanium dioxide
    0.15% by wt. zinc oxide
    90.52% by wt. white emulsion, including water, oil, and emulsifiers The above formulation, including CoQ10 in an aqueous emulsion, ensures that the product is white in color and remains white; and that the formulation provides a high level of anti-aging, antioxidant benefits that protect the skin from free radicals that damage the skin (DNA). The formulation will not streak on the skin or stain clothing, including white clothing. The amount of CoQ10 in this example is safe and effective.

D. 4% by wt. vanillin
    2.67% by wt. octyl salicylate
    2.67% by wt. octyl methoxycinnamate
    0.33% by wt. titanium dioxide
    0.15% by wt. zinc oxide
    90.52% by wt. white emulsion, including water, oil, and emulsifiers The above formulaion, using vanillin in an aqueous emulsion, ensures that the product is white in color and remains white; and that the formulation provides a high level of anti-aging, antioxidant benefits from free radicals that damage the skin (DNA), while also having the ability to tan the skin at a cellular level to a light golden brown within 4 to 8 hours of application and continuing to tan the skin for up to 24 hours. The formulation will not streak on the skin or stain clothing, including white clothing. The amount of vanillin in this example is safe and effective.

E. 4% by wt. CoQ10
    2.67% by wt. octyl salicylate
    2.67% by wt. octyl methoxycinnamate
    0.33% by wt. titanium dioxide
    0.15% by wt. zinc oxide
    88.25% by wt. white emulsion, including lime juice, lime oil, and emulsifiers The above formulation, using CoQ10 in a lime emulsion, ensures that the product is white in color and remains white; and that the formulation provides a high level of anti-aging, antioxidant benefits from free radicals that damage the skin (DNA). The formulation will not streak on the skin or stain clothing, including white clothing. The amount of CoQ10 in this example is safe and effective.

F. 4% by wt. vanillin
    2.67% by wt. octyl salicylate
    2.67% by wt. octyl methoxycinnamate
    0.33% by wt. titanium dioxide
    0.15% by wt. zinc oxide
    88.25% by wt. white emulsion, including lime juice, lime oil, and emulsifiers The above formulation, using vanillin in a lime emulsion, ensures that the product is white in color and remains white; and that the formulation provides a high level of anti-aging, antioxidant benefits from free radicals that damage the skin (DNA), while also having the ability to tan the skin to a light golden brown at a cellular level within 4 to 8 hours from applicationh and continuing for up to a period of 24 hours. The formulation will not streak on the skin or stain clothing, including white clothing. The amount of vanillin in this example is safe and effective.

As the result of further research I have found that a larger percentage, up to 45%, of vanillin in a lime juice, lime oil, white emulsion has the added benefit of enabling the skin to remain tanned for a longer period of time while not basically affecting the selected color for tanning, be it light, medium, or dark. My research has further shown that the vanillin, lime juice, lime oil white tanning emulsion can be applied for the dual purpose of getting a massage and a tan at the same time. The white tanning emulsion can be applied to the skin by a licensed massage therapist, or physical massage therapist during the massage process. The white tanning emulsion does not stain clothing, or bedding articles, and can therefore be used as a massage/tanning emulsion in a professional setting/environment. An individual would have the option of self-applying at their discretion.

The ability to get a tan and a massage at the same time does not currently exist in the marketplace. As the benefits of the white emulsion's tanning capabilities become known it could dramatically cut down on the cases of skin cancer. Tans resulting from the sun and tanning beds could be replaced with this non-cancerous, anti-oxidant, anti-aging, free radical fighting white formulation. No more unattractive sun tan lines on the skin to distract from one's overall appearance.

Also, an additional benefit of adding CoQ10 in the same white liquid vanillin, lime juice, lime oil emulsion further increases the non-cancerous, anti-oxidant, anti-oxidant benefits of the white non-staining formulation. CoQ10 exists in every cell in the body and has been studied for its benefit in topical formulations in fighting free radicals.

Example G

45% by wt. vanillin
3% by wt. CoQ10+SPF 15

5% by wt. octyl salicylate
6% by wt. octyl methoxycinnamate
0.75% by wt. titanium dioxide
1% by wt. zinc oxide
39% by wt. inactive ingredients, including lime emulsion Example H 35% by wt. vanillin+SPF 15
5% by wt. octyl salicylate
6% by wt. octyl methoxycinnamate
0.75% by wt. titanium dioxide
1% by wt. zinc oxide
52.25% by wt. inactive ingredients, including lime emulsion Dihydroxyacetone, known as DHA, is the most common and widely known ingredient used in sunless tanning products. It is considered safe according to the Food, Drug & Cosmetic Industry (FD&C). It has been used as an additive in the preparation of cosmetics for almost 30 years.

D-erythrulose, known as erythrulose, is used in some self-tanning cosmetics, in general, combined with dihydroxyacetone (DHA). Erythrulose takes 24 to 48 hours for a light tan color to completely develop on the skin.

Both DHA and erythrulose interact with the amino acids in dead skin cells to produce a tan color on the skin. But dead skin cells are constantly being shed, so the tan color produced by DHA and erythrulose normally lasts only a few days.

People who want a sunless tan prefer to see instant results. However, because DHA and erythrulose, used separately or in combination, take several hours to complete tanning of the skin, it became necessary to add colorants or dyes that immediately stain the skin, so that the customer sees an instant tan. The temporary effect of the dyes is gradually replaced by the more desirable tan produced by DHA and/or erythrulose. But the dyes stain all clothing, towels, or linens that they come in contact with. This unfortunate result is permanent and cannot be reversed.

Vanillin used for the purpose of sunless tanning penetrates the skin more deeply, at a cellular level below the dead skin cells. As the color develops in the stratum corneum and epidermis, it produces a longer lasting, more natural looking tan.

When vanillin is combined with DHA or erythrulose, or both, in sunless tanning products, without dyes, clothing can be worn immediately after application without the fear of permanently staining clothing, towels, or linens. In addition, the combination provides a more natural tan that lasts much longer.

DHA produces a basic tan color on dead skin cells within 2 to 4 hours of application. Vanillin produces a tan color change to the skin within 4 to 8 hours of application, and the color will continue to develop for up to 24 hours. Erythrulose produces a tan color change to the skin over a period of 24 to 48 hours after application.

The combination of vanillin with DHA or erythrulose, or both, in a sunless tanning formulation maximizes each ones unique tanning capability as they collectively provide a superior overall tanning result, without the use of colorants or dyes. More importantly, the exclusion of dyes enables the formulation of a white, color-stable tanning lotion, in accordance with the present invention.

The result is a white emulsion that provides a natural looking tan fully developed over a 24 hour time period; does not streak upon application; does not stain clothing; does not fade unevenly, and lasts from two to three weeks.

Vanillin is an anti-oxidant, anti-aging ingredient, in addition to its tanning effect. A formulation containing vanillin, DHA, and erythrulose is an anti-oxidant, anti-aging. tanning formulation. The present invention causes the formulation to remain white in color throughout the shelf life of the product.

Example

A. 3% by wt. erythrulose
4% by wt. dihydroxyacetone (DHA)
10% by wt. vanillin
4% by wt. octyl salicylate
4% by wt. octyl methoxycinnamate
0.50% by wt. titanium dioxide
0.23% by wt. zinc oxide
74.17% by wt. white emulsion, including water, oil, and emulsifier.

The percentages of erythrulose, DHA, and vanillin in the formulation can vary, depending on an individual's preferred shade of tan, light, medium, or dark. In order to obtain the desired tan color, the range of erythrulose is from 0.50% by wt. to 3% by wt., the DHA range is from 0.50% by wt. to 10% by wt., and the vanillin range is from 0.50% by wt. to 45% by wt. These percentages differ slightly when erythrulose or DHA is not present.

The percentage of octyl salicylate is from 1% by wt. to 15% by wt., the percentage of octyl methoxycinnamate is 1% by wt. to 15% by wt., titanium dioxide is from 0.15% by wt. to 5% by wt., and zinc oxide is from 0.15% by wt. to 5% by wt.

The lowest percentages of DHA and/or erythrulose, plus vanillin are also useful in a formulation for daily use, to provide maintenance of an existing tan, and to obtain the continuing benefit of anti-aging, anti-oxidant properties. Daily use for maintenance is never a practical option with products that stain clothing and linens.

Regardless of the percentages of erythrulose, DHA, or vanillin, the formulations remain white, and stain-free. Tanning will develop on the skin within the same time periods previously stated.

The invention claimed is:

1. A method for sunless tanning of skin comprising applying to selected areas of the skin a white, color-stable formulation consisting essentially of: (a) a concentration of vanillin adjusted to obtain the desired shade of tan; (b) an effective amount of dihydroxyacetone for tanning the skin; (c) a white emulsion consisting essentially of lime oil dispersed in lime juice and at least one emulsifier; and (d) effective amounts of octyl salicylate and octyl methoxycinnammate for color stabilization.

2. The method of claim 1 further comprising:
about 0.15 to 5.0 wt % titanium dioxide, and
about 0.15 to 5.0 wt % zinc oxide.

3. The method of claim 1 further comprising: a benzoquinone.

4. The method of claim 1 further comprising: at least one sunscreen in amounts sufficient to provide an SPF rating of at least 15.

5. The method of claim 2 further comprising: a benzoquinone.

6. The method of claim 1 further comprising: an effective amount of d-erythrulose for tanning the skin.

7. The method of claim 1 wherein said white emulsion contains about 64 wt % to about 84 wt % lime juice.

8. The method of claim 7 further including effective amounts of zinc oxide and titanium dioxide for color stabilization.

* * * * *